United States Patent [19]

Kratzer et al.

[11] 4,316,035
[45] Feb. 16, 1982

[54] PREPARATION OF PERFLUORINATED 1,2,4-OXADIAZOLES

[76] Inventors: Robert A. Frosch, Administrator of the National Aeronautics and Space Administration, with respect to an invention of Reinhold H. Kratzer, Irvine, Calif.; Kazimiera J. L. Paciorek, Corona del Mar, Calif.; Thomas I. Ito, Fountain Valley, Calif.; Robert W. Rosser, San Jose, Calif.

[21] Appl. No.: 163,838

[22] Filed: Jun. 27, 1980

[51] Int. Cl.$^3$ .............. C07D 271/06; C08G 73/06
[52] U.S. Cl. ................................. 548/131; 528/401; 528/422; 564/229
[58] Field of Search ............................... 528/401, 131

[56] References Cited

U.S. PATENT DOCUMENTS 4,145,524  3/1979  Frosch .............................. 548/131

OTHER PUBLICATIONS

Clapp, Advances in Heterocyclic Chemistry, vol. 20, (Academic Press, 1976), pp. 66-71.

*Primary Examiner*—Alton D. Rollins
*Attorney, Agent, or Firm*—Darrell G. Brekke; John R. Manning

[57] ABSTRACT

Fluorinated alkyl or alkylether 1,2,4-oxadiazole compounds are prepared by cyclizing the corresponding alkyl or alkylether imidoylamidoximes in vacuo or in an inert atmosphere at a temperature within the range of 40° to 100° C. for a period of 8 to 144 hours in the presence of an acid compound which can accept ammonia to form a salt. The imidoylamidoximes usable in this process may be either polymeric or nonpolymeric. The products, when polymeric, have excellent heat, chemical and solvent resistance.

4 Claims, No Drawings

PREPARATION OF PERFLUORINATED 1,2,4-OXADIAZOLES

ORIGIN OF THE INVENTION

The invention described herein was made in the performance of work under a NASA contract and is subject to the provisions of Section 305 of the National Aeronautics and Space Act of 1958, Public Law 85-568 (72 Stat. 435; 42 U.S.C. 2457).

TECHNICAL FIELD

This invention relates to perfluorinated 1,2,4-oxadiazoles and to an improved process for making them.

BACKGROUND ART

Heat and chemical resistant polymers characterized by perfluorinated segments joined by 1,2,4-oxadiazole linkages have been disclosed by Rosser et al. in U.S. Pat. No. 4,145,524. These polymers are made by a condensation process involving a perfluorinated diamidoxime, $R_f[C(NH_2)=NOH]_2$. The condensation is carried out at a temperature within the range of 100° to 250° C., preferably between 130° and 200° C. either in vacuo or in an inert atmosphere, to yield gaseous products and polymers of the formula

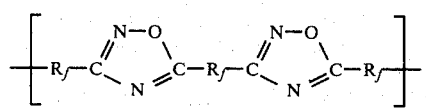

in which x is of a magnitude commensurate with a molecular weight range 3,000 to 50,000. The diamidoxime from which these polymers are made is obtained originally by the following reaction which normally takes place at ambient temperature:

For many applications, it would be advantageous to prepare the 1,2,4-oxadiazole polymers by a more articulated process that could be better controlled and could yield improved polymers.

An object of this invention is to provide a process by which 1,2,4-oxadiazoles can be synthesized at temperatures significantly lower than those used in the art. Another object is to provide a process which minimizes or avoids the side reactions and the partial decomposition of the reactants that lead to shorter polymeric chains and to random creation of linkages other than oxadiazole linkages. Still another object is to provide a process capable of higher yields than the processes of the art.

DISCLOSURE OF THE INVENTION

These and other ojbects of this invention have been achieved by heating an imidoylamidoxime at temperatures within the range of 40° to 100° C. for a period of 8 to 144 hours in the presence of an acid compound which acts as an ammonia acceptor. The reaction involved is:

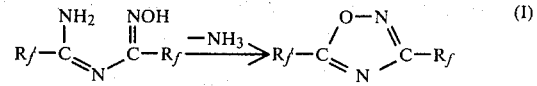

The imidoylamidoximes that can be so treated can be either simple perfluorinated compounds containing only one imidoylamidoxime group or they can be polymeric substances containing many such imidoylamidoxime groups as linkages.

The imidoylamidoximes have been disclosed in copending application Ser. No. 163,839, filed June 27, 1980. They are produced by allowing to react together at temperatures within the range of 20° to 70° C. a perfluorinated alkyl or alkylether nitrile with a perfluorinated alkyl or alkylether amidoxime as illustrated by the following reaction:

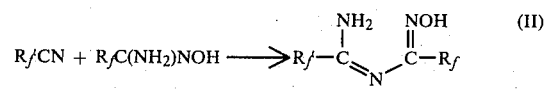

When the nitrile and the amidoxime compounds selected are bifunctional, oligomeric or polymeric products will be yielded by reactions I and II, depending on actual reaction conditions employed.

DETAILED DESCRIPTION OF THE INVENTION

Cyclization reaction I is carried out in an inert atmosphere or in vacuo, preferably at temperatures within the range of 40° to 100° C. in the presence of an acid compound that acts as an ammonia acceptor. Usable compounds for this function include organic acids, inorganic acids, anhydrides, acyl and aryl halides, and more specifically, fatty acids, fluorinated fatty acids, perfluorinated alkylether acids such as $C_2F_5(OCF_2CF_2)_nCOOH$, $C_3F_7O[CF(CF_3)CF_2O]_nCF(CF_3)COOH$, sulfuric acid, phosphoric acid, phosphorus pentoxide, and the like.

The substituents $R_f$ and $R_f'$ in the nitriles and amidoximes used to carry out the present invention can be identical or different and are selected (a) from the monovalent perfluoroalkyl and perfluoroalkylether radicals represented by the general formulas: $C_nF_{2n+1}—$, $C_2F_5(OCF_2CF_2)_nOCF_2—$, $C_3F_7O[CF(CF_3)CF_2O]_nOCF(CF_3)—$, or when dinitriles and diamidoximes are required, (b) from bivalent radicales such as $—(CX_2)_p—$, arylene, $—CFY(OCF_2CFY)_mO(CX_2)_pO(CFYCF_2O)_nCFY—$, and the like, in which p ranges from 2 to 8 when X is fluorine and 2 to 18 when X is hydrogen, Y is fluorine or a trifluoromethyl group or an assortment of such substituents, and m+n ranges from 2 to 7.

A few specific embodiments will now be provided to further illustrate the invention in operational detail. These examples are not intended to be limiting, unless otherwise specified.

EXAMPLE 1

The amidoxime $C_3F_7OCF(CF_3)CF_2OCF(CF_3)C(=NOH)NH_2$ (1.00 g, 1.97 mmol) and the nitrile $C_3F_7OCF(CF_3)CN$ (1.50 g, 4.82 mmol) were sealed in vacuo and heated at 50° C. for 89 hours. After opening the container and removing the excess nitrile (2.81 mmol) in vacuo at 50° C., the corresponding imidoylamidoxime ($C_{15}H_3F_{28}N_3O_4$) was obtained in the pure state in quantitative yield, as determined inter alia by elemental analysis.

EXAMPLE 2

The bisamidoxime $H_2N(HON=)CCF(CF_3)[OCF_2CF(CF_3)]_m$—$O(CF_2)_5O[CF(CF_3)CF_2O]_nCF(CF_3)C(=NOH)NH_2$ in which m+n=3 (0.63 g, 0.60 mmol) was heated with the corresponding dinitrile (0.66 g, 0.64 mmol) at 50° C. for 52 hours with stirring. The infrared spectrum of the viscous liquid product, which had a molecular weight of 4300, showed the characteristic absorbances for imidoylamidoxime moieties. No significant nitrile and amidoxime absorption could be detected. Elemental analysis of the product gave: C, 22.75%; H, 0.63%; F, 63.03%; and N, 3.93%. These values substantially agree with contents calculated for formula $C_{80.46}H_{14.89}F_{144.84}N_{12.89}O_{25.14}$, a compound with a molecular weight of 4315.99.

EXAMPLE 3

In a typical preparation of an oxadiazole, equimolar quantities of the imidoylamidoxime, e.g. $C_3F_7OCF(CF_3)CF_2OCF(CF_3)C(=NOH)N=C(NH_2)CF(CF_3)OC_3F_7$, and a given ammonia acceptor were heated at a specific temperature for a given period of time under nitrogen bypass. At the conclusion of this procedure, trichlorotrifluoroethane (Freon 113) was added to the reaction mixture to form a slurry, which was filtered to remove the ammonium salt produced. After removal of the solvent, the oxadiazole yield was determined by gas chromatography, utilizing for compound quantitation, a flame ionization detector, and for compound identification, a mass spectrometer. The ammonia acceptor, the reaction conditions and the yield of oxadiazole are shown in the table below.

TABLE

Yield of

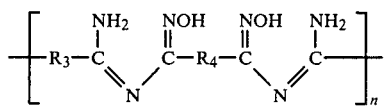

| Ammonia Acceptor | Temp. (°C.) | Time Period (Hour) | Oxadiazole Yield (%) |
| --- | --- | --- | --- |
| $C_7F_{15}COOH$ | 70 | 19 | 71 |
| $C_7F_{15}COOH$ | 110 | 17 | 49 |
| $CF_3COOH$ | 70 | 20 | 25 |
| $R_fCOOH^a$ | 70 | 24 | 49 |
| $H_2SO_4$, conc. | 70 | 24 | 13 |
| $H_3PO_4$, conc. | 70 | 90 | 52 |
| $P_2O_5$ | 70 | 91 | 46 |

$^aR_f = C_3F_7O[CF(CF_3)CF_2O]_2CF(CF_3)$—

As these results demonstrate, a variety of organic and inorganic acidic compounds may be employed to absorb the ammonia and facilitate the cyclization of the imidoylamidoximes. It is also evident that carrying out the reaction at a temperature of 110° C. rather than 70° C. can actually lower the yield of 1,2,4-oxadiazole, in this instance, from 71% to 49%.

EXAMPLE 4

The polyimidoylamidoxime of Example 2 (0.35 g, 0.33 mmol) was stirred and heated with n-perfluorooctanoic acid (0.14 g, 0.34 mmol) at 70° C. for 29 hours. Trichlorotrifluoroethane (Freon 113), 5 ml, was added to form a slurry, which was filtered to remove the ammonium octanoate formed by the reaction. After removal of the solvent and drying in vacuo at 68° C. for 4 hours, a quantitative yield of the corresponding polyoxadiazole was obtained. Analysis of the product showed an elemental content of 22.44% C, 0.56% H, 62.87% F, and 3.30% N substantially agree with contents calculated for formula $C_{60.73}H_{5.82}F_{109.31}N_{7.89}O_{19.22}$ of the oxadiazole polymer. The viscous material had a molecular weight of 2600 and showed no infrared absorbance at 6.0μ, thus indicating complete transformation of the imidoylamidoxime linkages.

A great advantage of the imidoylamidoxime route to 1,2,4-oxadiazoles is especially evident in the formation of polymers from difunctional nitriles and difunctional amidoximes. In such instances, the lower cyclization reaction temperatures that the imidoylamidoximes permit, avoid the side reactions caused by the decomposition of the diamidoximes used in the art U.S. Pat. No. 4,145,524), resulting in a better polymeric product which contains fewer shorter chains that would otherwise be present.

The imidoylamidoximes prepared by the new low temperature condensation process disclosed can serve either as chain stoppers or crosslink index diluters in certain polymerization reactions, or, when they are oligomeric or polymeric, they can be converted to useful polyoxadiazoles of the type described in U.S. Pat. No. 4,145,524. Such heat and chemical resistant polymers, when suitably compounded with fillers, extenders, and modifiers, can be used in numerous applications in which high stability, impermeability to liquids and gases, and good plasticity are advantageous, e.g. as adhesives, caulking compounds, channel sealants, and fuel tank liners.

It will be readily apparent, furthermore to one of ordinary skill in the art that many changes and modifications can be made in the process and the products described, without departing from the spirit and the scope of the following claims.

It is claimed:
1. A process for preparing 1,2,4-oxadiazoles and polymers thereof which comprises:
   (a) providing an imidoylamidoxime selected from the class consisting of

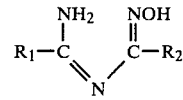

and

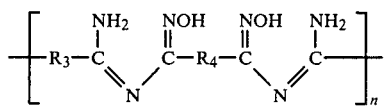

wherein
$R_1$ and $R_2$ are the same or different and are selected from the class consisting of (a) perfluoroalkyl and (b) perfluoroalkyl ether,
$R_3$ and $R_4$ are the same or different and are selected from the class consisting of perfluoroalkylene and perfluoroalkylene ether and
n is a positive integer,
   (b) heating such imidoylamidoximes within the range of 40° to 100° C. for a period of 8 to 144 hours in the presence of an ammonia acceptor whereby the imidoylamidoxime group or groups are converted to 1,2,4-oxadiazole groups.

2. The process of claim 1 wherein the ammonia acceptor is selected from the group consisting of aliphatic acids, fluorinated aliphatic acids, alkylether acids, fluorinated alkylether acids, concentrated sulfuric acid, concentrated phosphoric acid and phosphorus pentoxide.

3. The process of claim 1 wherein the imidoylamidoxime is the compound 1 and the product has the structure

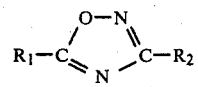

4. The process of claim 1 wherein the imidoylamidoxime is the polymer 2 and the product has the structure

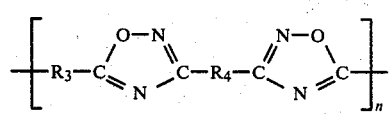

* * * * *